(12) United States Patent
Farmer et al.

(10) Patent No.: US 10,380,320 B2
(45) Date of Patent: Aug. 13, 2019

(54) DATA RESTRUCTURING FOR CONSISTENT FORMATTING

(71) Applicant: Passport Health Communications, Inc., Franklin, TN (US)

(72) Inventors: Richard W. Farmer, Nashville, TN (US); Donavon R. Feenstra, Cane Ridge, TN (US)

(73) Assignee: PASSPORT HEALTH COMMUNICATIONS, INC., Franklin, TN (US)

( * ) Notice: Subject to any disclaimer, the term of this patent is extended or adjusted under 35 U.S.C. 154(b) by 619 days.

(21) Appl. No.: 13/757,282

(22) Filed: Feb. 1, 2013

(65) Prior Publication Data

US 2013/0204642 A1 Aug. 8, 2013

Related U.S. Application Data

(60) Provisional application No. 61/594,459, filed on Feb. 3, 2012, provisional application No. 61/596,575, filed on Feb. 8, 2012.

(51) Int. Cl.
*G06F 19/00* (2018.01)
*G06Q 50/22* (2018.01)

(52) U.S. Cl.
CPC .......... *G06F 19/328* (2013.01); *G06Q 50/22* (2013.01)

(58) Field of Classification Search
CPC ...... G06Q 50/24; G06Q 50/22; G06F 19/322; G06F 19/328; G06F 19/3443; G06F 17/30672; G06F 17/30864
USPC .......................................................... 705/3
See application file for complete search history.

(56) References Cited

U.S. PATENT DOCUMENTS

| | | | |
|---|---|---|---|
| 8,260,634 B1 | 9/2012 | Lawlor | |
| 8,321,284 B2 | 11/2012 | Clements et al. | |
| 8,326,656 B2 | 12/2012 | Beery et al. | |
| 8,447,627 B1 | 5/2013 | Cruise | |
| 8,781,850 B2 | 7/2014 | Bazzani et al. | |
| 9,324,111 B2 | 4/2016 | Long | |
| 2004/0078236 A1* | 4/2004 | Stoodley | G06Q 50/22 705/2 |

(Continued)

OTHER PUBLICATIONS

Pennsylvania Department of Health, Health Level Seven version 2.3.1, Dec. 1, 2005.*

(Continued)

*Primary Examiner* — Reginald R Reyes
(74) *Attorney, Agent, or Firm* — Merchant & Gould

(57) ABSTRACT

Consistently coded eligibility data is provided. Eligibility responses may be received from various payers comprising inconsistently coded eligibility benefit (EB) information provided in EB segments in various locations in the responses. A data restructuring engine may be operable to receive an eligibility response and restructure the response into a consistent format. Co-pay, co-insurance, benefit limitations, and benefit specific deductibles may be clarified by embedding coded strings in one or more message segments attached to EB segments. Service types, network indicators, place of service codes, and message text may be removed when a coded strings is created. Recoded eligibility responses may be provided to healthcare providers, providing coverage, eligibility, and benefit data in a consistent and standardized form, regardless of the payer sending the eligibility response.

18 Claims, 5 Drawing Sheets

(56) References Cited

U.S. PATENT DOCUMENTS

| | | | |
|---|---|---|---|
| 2005/0216250 A1* | 9/2005 | Simmon | H04L 67/2823 |
| | | | 703/27 |
| 2006/0235881 A1* | 10/2006 | Masarie | G06F 17/278 |
| 2007/0005564 A1* | 1/2007 | Zehner | 707/2 |
| 2007/0050219 A1 | 3/2007 | Sohr et al. | |
| 2007/0124310 A1* | 5/2007 | Mathur | G06F 21/6245 |
| 2007/0185390 A1* | 8/2007 | Perkins | A61B 5/0002 |
| | | | 600/300 |
| 2009/0094055 A1* | 4/2009 | Gage, Jr. | G06F 19/328 |
| | | | 705/2 |
| 2010/0036676 A1* | 2/2010 | Safdi | G06F 19/321 |
| | | | 705/2 |
| 2010/0121656 A1 | 5/2010 | Andros et al. | |
| 2010/0274594 A1* | 10/2010 | Virdhagriswaran | G06Q 10/10 |
| | | | 705/4 |
| 2011/0251857 A1 | 10/2011 | Thorne et al. | |
| 2012/0191730 A1 | 7/2012 | Parikh et al. | |
| 2012/0203853 A1 | 8/2012 | Davis et al. | |
| 2013/0060576 A1* | 3/2013 | Hamm | G06F 19/3418 |
| | | | 705/2 |
| 2013/0204642 A1* | 8/2013 | Farmer | G06F 19/328 |
| | | | 705/3 |
| 2014/0164026 A1 | 6/2014 | Long et al. | |

OTHER PUBLICATIONS

Office Action dated May 1, 2015, in U.S. Appl. No. 14/099,804.
Office Action dated Nov. 21, 2014, in U.S. Appl. No. 14/099,804.
Notice of Allowance dated Dec. 18, 2015, in co-pending U.S. Appl. No. 14/099,804.

* cited by examiner

DATA RESTRUCTURING FOR CONSISTENT FORMATTING

CROSS-REFERENCE TO RELATED APPLICATIONS

The present application claims priority to U.S. Provisional Patent Application No. 61/594,459 titled "Data Restructuring for Consistent Formatting" filed Feb. 3, 2012, and U.S. Provisional Patent Application No. 61/596,575 titled "Data Restructuring for Consistent Formatting" filed Feb. 8, 2012, the disclosures of which are incorporated herein by reference in their entireties.

BACKGROUND

When a patient seeks healthcare services from a healthcare provider, the provider may request information from a payer (e.g., insurance company) to determine if the patient is eligible to receive benefits for healthcare services; and if the patient is eligible, the provider may request other benefit and eligibility information such as benefit amounts, co-insurance, co-pays, deductibles, exclusions, and limitations related to a specific procedure. The request for information may be sent as an eligibility request, for example, a 270 request or transaction. A payer may communicate eligibility benefit information associated with a subscriber or dependent in a response, for example, a 271 response or reply.

The eligibility request and response may be required to meet processing standards. For example, eligibility transactions may be sent in an X12 syntax format and may be coded and structured according to standards established by the Secretary of Health and Human Services (HHS) as required by the Health Insurance Portability and Accountability Act of 1996 (HIPAA). As is known in the art, HIPAA includes provisions for administrative simplification and support electronic exchange of administrative and financial healthcare transactions primarily between healthcare providers and plans. As should be appreciated, embodiments may be utilized with other formats, structures, and syntaxes according to changes in healthcare laws. For example, a 270 eligibility request may be replaced by an eligibility request of another format and utilizing an alternate syntax. A 271 response may be replaced by an eligibility response of another format and utilizing an alternate syntax.

Healthcare eligibility transaction sets may be designed to satisfy needs of a simple eligibility status inquiry (e.g., is a subscriber/dependent eligible?). When a request is made for more complex information (e.g., benefit amounts, co-insurance, co-pays, deductibles, exclusions, and limitations related to a specific procedure), the content of eligibility responses may vary depending on a level of data made available by an information source.

Implementation guides may be provided so that health plans, providers, clearinghouses, and software vendors may be able to ready their information systems and applications software for compliance with the standards; however, some transmission formats may not be specific enough to provide enough structure for an eligibility response to be able to guarantee that, for example, a healthcare provider will be able to find a specific piece of information in a specific place. While some consistent usage of standards, including loops, segments, data elements, etc. across all guides is used to support standardization, ambiguities and variations may arise in eligibility responses due to an imprecise nature of an implementation guide, for example, the X12 implementation guides adopted by HIPAA. According to one example, the X12 format may require an input of a deductible amount in a specific eligibility benefit segment of a 271 response; however, the format may not require for the input to be a specific input type (e.g., dollar amount vs. percentage, etc.). A healthcare provider may receive a 271 response from one payer with a deductible amount in a dollar format and a 271 response from another payer with a deductible amount in a percentage format. As can be appreciated, receiving 271 responses in inconsistent formats can be inefficient, frustrating, and may lead to errors.

Additionally, service codes used in an eligibility response may be inexact and limited. For example, only simple provider/payer/patient relationships may be coded in compliance with HIPAA, causing an overlap between place of service codes and service type codes. Payers may use a degree of latitude in selecting which HIPAA code values to use. Minimal restrictions within implementation guides may allow payers to use various code values when coding the same information. Accordingly, an eligibility response may be standards-compliant yet still require extensive analysis by a healthcare provider to understand the actual benefits. While a historical assumption is that a 271 response may be processed as a human readable response, not as a machinable transaction whose data content may be utilized to drive software processes downstream, current systems do not provide for highly consistent responses that match formatting of other payers' 271 responses.

It is with respect to these and other considerations that the present invention has been made.

SUMMARY

The above and other problems are solved by organizing eligibility benefit information into a consistently coded format. Embodiments may be utilized to receive eligibility benefits from one or more disparate sources and to restructure the information into a consistent format. Embodiments may provide for parsing an eligibility response for place of service information, service type information, provider type information, relation of provider to payer information, relation of provider to patient information, reason for service information, service category information, free-form message text identifying critical benefit details, and free-form message text identifying benefit details identified in an eligibility benefit segment. One or more coded strings may be created, a coded string comprising a tag, a "place of service" dimension, a "service type" dimension, a "provider type" dimension, a "relation of provider to payer" dimension, a "relation of provider to patient" dimension, a "reason for service" dimension, and a "service category" dimension, each dimension separated by a separator. A recoded eligibility response comprising the one or more coded strings may be created and sent to a healthcare provider.

The details of one or more embodiments are set forth in the accompanying drawings and description below. Other features and advantages will be apparent from a reading of the following detailed description and a review of the associated drawings. It is to be understood that the following detailed description is explanatory only and is not restrictive of the invention as claimed.

DETAILED DESCRIPTION

Figure 1:
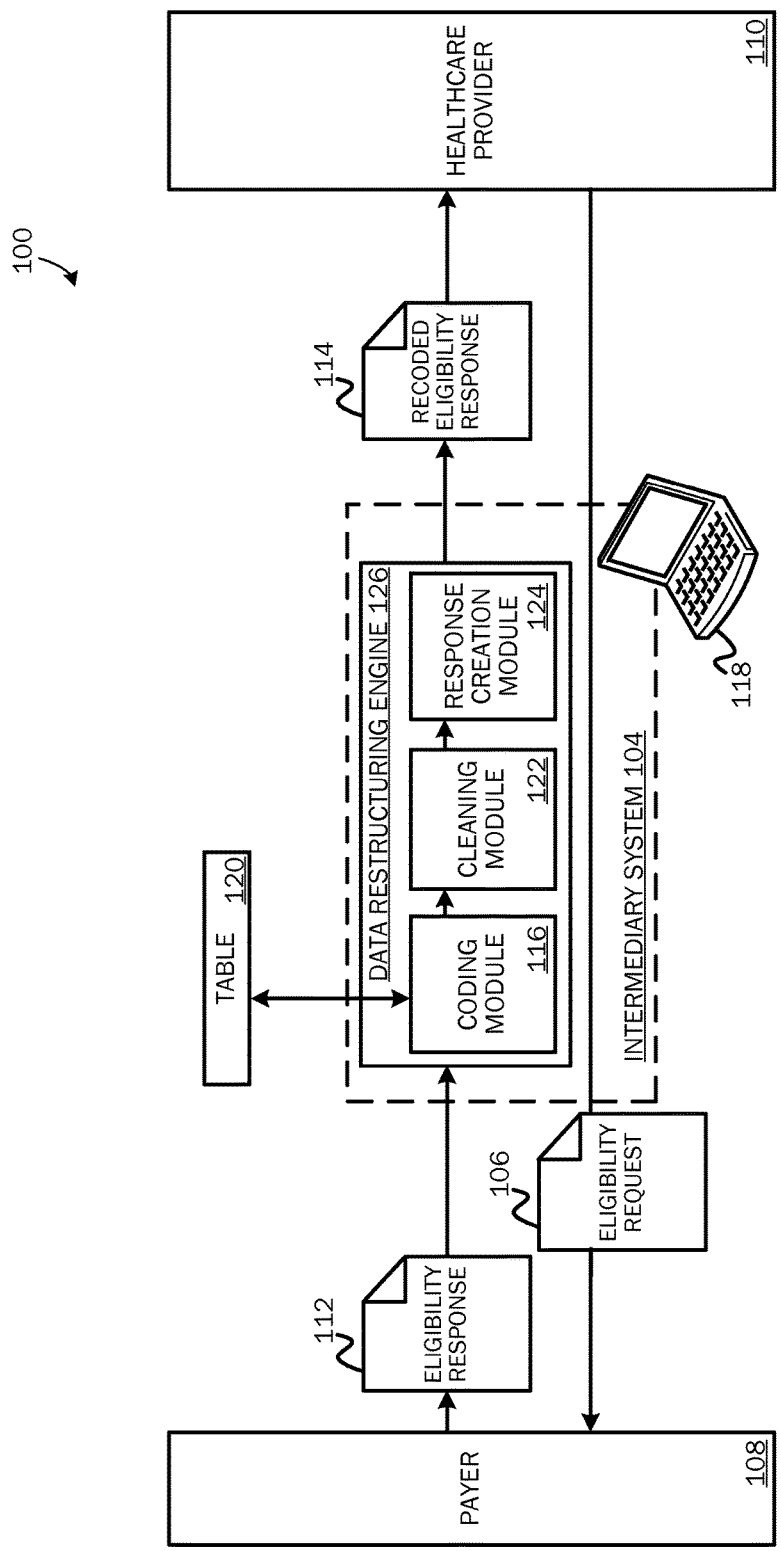
FIG. 1 is a simplified block diagram of one embodiment of a system including a coding module, a cleaning module, and a response creation module.

As described herein, embodiments provide for consistently coded eligibility data. Eligibility responses, for example, 271 responses, may be received from various payers comprising inconsistently coded eligibility benefit (EB) information provided in EB segments in various locations in the eligibility responses. A coding module, a cleaning module, and a response creation module may be provided, the modules operable to receive an eligibility response, and restructure the response into a consistent format. Co-pay, co-insurance, benefit limitations, and benefit specific deductibles may be clarified by embedding coded strings in one or more message segments attached to EB segments. Service types, network indicators, place of service codes, and message text may be removed when a coded strings is created. Recoded eligibility responses may be provided to healthcare providers, providing coverage, eligibility, and benefit data in a consistent and standardized form, regardless of the payer sending the eligibility response.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

As described briefly above, eligibility benefit information may be transmitted between payers and the healthcare provider community in a standard format according to healthcare laws, for example, HIPAA. Eligibility benefit information associated with a subscriber or dependent may be communicated in an eligibility response, for example, a 271 response or reply. Oftentimes, some specifications may be too broad to be useful by the end consumer of the data. For example, current standards may not specify how or where to include certain information in an eligibility response (e.g., co-payment amount for healthcare services provided for an illness versus an injury). Accordingly, a payer may include benefit detail information in message segments to overcome electronic data interchange (EDI) standards shortfalls. Additionally, minimal restrictions within implementation guides allow payers to use latitude in selecting which code values to use, resulting in various coding of the same information. For example, a 271 response may be HIPAA compliant and still require extensive analysis to understand a subscriber or dependent's eligibility benefits.

Referring now to FIG. 1, a simplified block diagram of a high-level system architecture 100 with which embodiments of the invention may be implemented is illustrated. The system 100 may include an information requester (referred to herein as a healthcare provider 110). The healthcare provider 110 may request information about healthcare coverage eligibility and benefits associated with a health plan subscriber or dependent of a health plan subscriber. The request for information may be in the form of an eligibility, coverage, or benefit inquiry 106. The eligibility inquiry 106 may be sent directly to a responder (referred to herein as a payer 108) or alternatively, may be sent to a payer 108 via an intermediary system 104. Because there are many different ways to communicate with various players in a healthcare system, an intermediary system 104 may be utilized to normalize communication solutions, data requirements, and transaction formats for their business partners.

As described above, an eligibility response 112 may be utilized to respond to an eligibility request 106 with coverage, eligibility, and benefit information. The eligibility response 112 may be received by the sender, which may be the intermediary system 104 or the healthcare provider 110. According to embodiments, the system 100 may comprise data restructuring engine 126. In the illustrated embodiment, the data restructuring engine 126 is executed on a computing device 118. An eligibility response 112 may be restructured into a recoded eligibility response 114 by a coding module 116, a cleaning module 122, and a response creation module 124.

The coding module 116, cleaning module 122, and response creation module 124 of the data restructuring engine 126 may be operable to receive an eligibility response 112, parse data within the eligibility response 112, and provide consistent benefit coding via a coded string in a message segment. The data restructuring engine 126 may also be operable to remove data elements in the eligibility response 112 replaced by the coded string and reformat the eligibility response 112 into a recoded eligibility response 114 that can be effectively used by healthcare provider systems 110.

The recoded eligibility response 114 may be a machine-readable response. According to an embodiment, an intelligent receiving system may be utilized by a healthcare provider 110 to render the data in the recoded eligibility response 114 into a human readable format. Although the data restructuring engine 126 is illustrated as located at the intermediary system 104, the coding module 116, the cleaning module 122, and the response creation module 124 may be implemented within a healthcare provider system 110 or may be located remotely and accessed via a network. The coding module 116, the cleaning module 122, and the response creation module 124 may be implemented using one or more computing devices.

According to embodiments, the data restructuring engine 126 may modify an eligibility response 112 to reformat data within the response into a consistent format where a healthcare provider 110 may be able to find the information they are looking for more efficiently without having to read through an entire set of data. Additionally, downstream processes (e.g., estimators and database loading functions) may be enabled to perform accurately without having to adjust for idiosyncrasies of a specific payer 108 who sourced the data.

Embodiments may provide for a cleaning process and modifications of the data to be performed. For example, if a payer 108 sends the same benefit information twice, the duplicate piece of information may be filtered out. As another example, a received eligibility response 112 may include extra data that may not be applicable. The eligibility response 112 may include an individual co-pay amount (as opposed to a family co-pay amount); however, the individual co-pay may be the same as the family co-pay. Thus, the additional information (individual versus family) does not need to be included. Embodiments may filter out the extraneous data.

Embodiments also provide for consistent benefit coding. When providing consistent benefit coding, values in certain data elements or eligibility benefit (EB) segments may be removed and replaced with a coded string in a message segment. According to embodiments, co-pay, co-insurance, benefit limitations, and benefit specific deductibles may be clarified, and consistent benefit coding may be embedded into one or more message segments attached to EB segments within a recoded eligibility response 114.

The system 100 may include one or more tables 120 which may be generated from historic transaction data. The coding module 116 may utilize the table 120 to learn where to find specific data from a specific payer 108. The coding module 116 is capable of learning locations for specific pieces of information. Additionally, the coding module 116 may utilize historic transaction data to provide information that may not be included in an eligibility response 112. For example, a 271 response 112 may include information that a subscriber's plan may include a co-insurance amount of zero dollars for an MRI. Historic transaction data may include information that the subscriber's plan may include a co-insurance amount of zero dollars for an MRI, but that the zero dollar co-insurance amount may only be applicable to outpatient hospital services. The coding module 116 may include the additional information into a recoded eligibility response 114 although the information was not included in the original eligibility transaction 112. The additional information may be beneficial to the receiving party (e.g., healthcare provider 110 or the subscriber) to better understand the scope of the subscriber's eligibility benefits.

Figure 2:
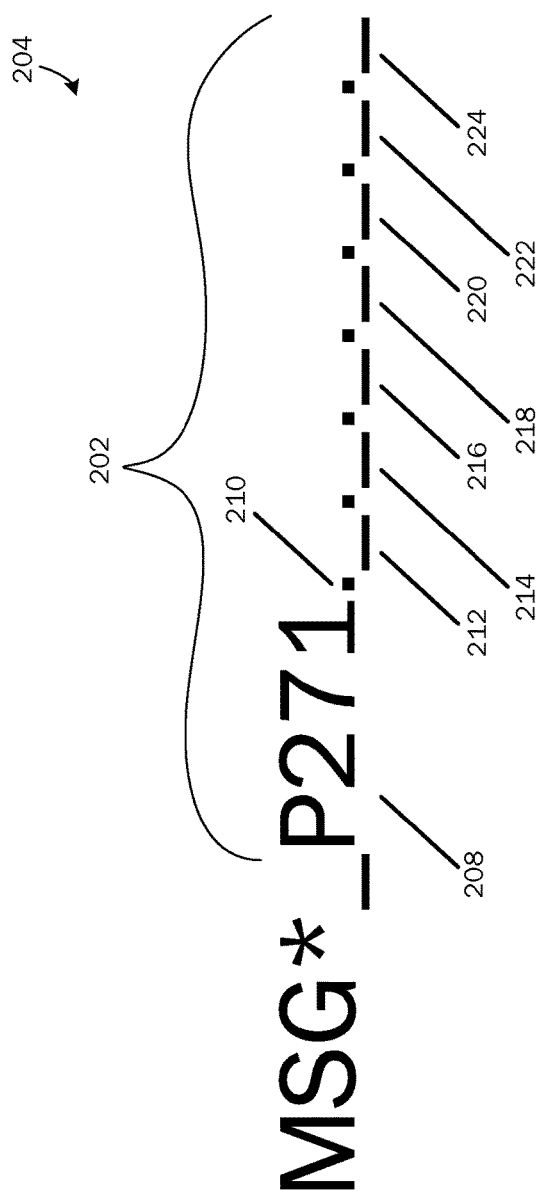
FIG. 2 is an illustration of a message segment of a recoded eligibility response.

Referring now to FIG. 2, a message segment 204 comprising a coded string 202 is illustrated. A message segment 204 in a recoded eligibility response 114 may include a tag 208 indicating that the eligibility response 114 has been recoded and the message segment 204 may include a coded string 202. The tag 208 may also provide information indicating whether the coded string 202 includes inclusion or exclusion information. For example, a tag 208 may include "_P271" if the coded string 202 in the message segment 204 comprises inclusion information and may include "_P271x" if the coded string 202 comprises exclusion information. For example, as illustrated in FIG. 3, a recoded eligibility response 114A comprises a tag 208 indicating that the message segment 204 includes a coded string 202 and that the coded string 202 includes inclusion information.

Figure 3:
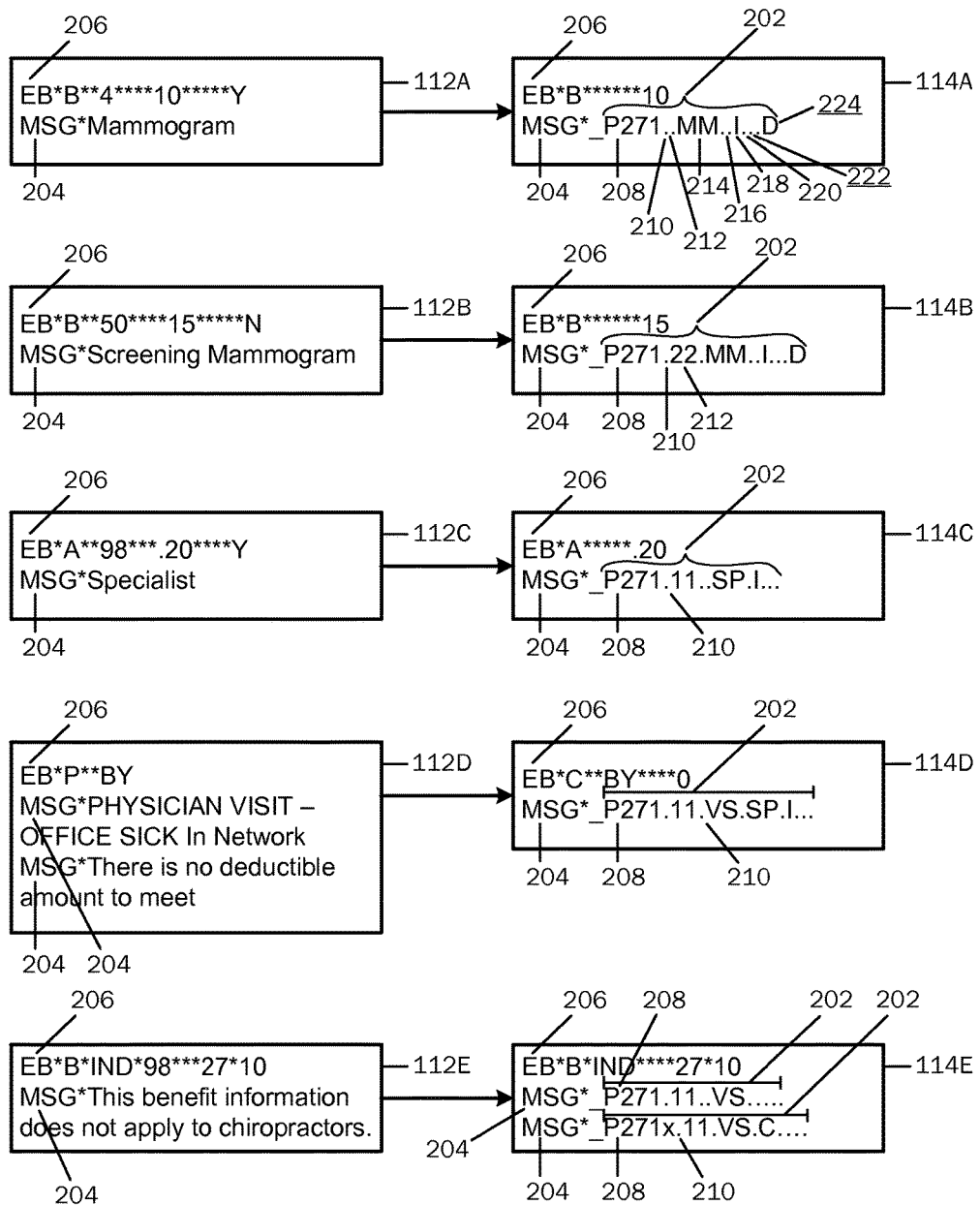
FIG. 3 is an illustration of example eligibility responses before and after reformatting.

As illustrated in an example recoded eligibility response 114E in FIG. 3, multiple messages 204 may be utilized in a recoded eligibility response 114 if a benefit has inclusions and exclusions. A payer 108 may report in an eligibility response 112 that a benefit excludes a certain provider type (e.g., chiropractic). As illustrated in the example eligibility response 112E, the payer 108 may provide exclusion information in a message segment 204 of the eligibility response 112. According to embodiments, to provide consistent coding, when a payer 108 provides exclusion information, both the included and excluded information may be provided in a recoded eligibility response 114. The first message segment 204 in the example recoded eligibility response 114E comprises a tag 208 indicating that the coded string 202 includes inclusion information. For example, the coded string 202 of the first message segment may be decoded to read that benefits may be provided for a $10 co-pay per visit at a professional (physician) office. The second message segment 204 in the example recoded eligibility response 114E comprises a tag 208 indicating that the coded string 202 includes exclusion information. For example, the coded string 202 of the second message segment 204 may be decoded to read that benefits may be provided for a $10 co-pay per visit for an office visit for all physicians except a chiropractic office.

With reference back to FIG. 2, according to embodiments, a coded string 202 may include various code values, each code value representing a dimension of a benefit. According to one embodiment, a coded string 202 may cover seven dimensions including a "place of service" dimension 212, a "service type" dimension 214, a "provider type" dimension 216, a "relation of provider to payer" dimension 218, a "relation of provider to patient" dimension 220, a "reason for service" dimension 222, and a "service category" dimension 224. A separator 210, for example, a period, may be inserted between dimensions in a coded string 202. According to embodiments, not all dimensions may be used for each benefit. Oftentimes, one or more of the dimensions may not be needed. This may imply that all aspects of that dimension may be covered. For example, many hospital in-patient services may not be broken down by a "service category" (e.g., diagnostic or screening). Accordingly, a code value for the "service category" dimension 224 may not be included in the coded string 202.

According to an embodiment, if a dimension does not have a value, a code value may not be inserted between the separators 210. For example, as illustrated in the example recoded eligibility response 114A in FIG. 3, the coded string 202 in the message segment 204 of the recoded eligibility response 114A does not have a code value after the separator 210 following the tag 208 (the "place of service" dimension 212). Accordingly, the coded string 202 may be decoded to read that all aspects of the "place of service" dimension 212 may be covered. That is, the patient's plan may cover a particular service at any location. An example of a message segment 204 comprising a "place of service" dimension 212 code value is illustrated in the example recoded eligibility response 114B. A "22" is included in the "place of service" dimension 212, which may be decoded to read that benefits may be provided for services rendered at an outpatient hospital setting. According to embodiments, "place of service" dimension 212 code values may be based on the "place of service" codes supported by Centers for Medicare and Medicaid Services (CMS) for claims processing and referenced in HIPAA with a seldom-used III segment. Additional codes may be utilized to support additional payer 108 definitions of places of service. A listing of example "places of service" and their corresponding code values includes:

| | |
|---|---|
| 01 | Pharmacy |
| 11 | Office |
| 12 | Home |
| 13 | Assisted Living Facility |
| 14 | Group Home |
| 15 | Mobile Unit |
| 20 | Urgent Care Facility |
| 21 | Inpatient Hospital |
| 22 | Outpatient Hospital |
| 23 | Emergency Room - Hospital |
| 24 | Ambulatory Surgical Center |
| 25 | Birthing Center |
| 26 | Military Treatment Facility |
| 31 | Skilled Nursing Facility |
| 32 | Nursing Facility |
| 33 | Custodial Care Facility |
| 34 | Hospice |

| | |
|---|---|
| 41 | Ambulance - Land |
| 42 | Ambulance - Air or Water |
| 49 | Independent Clinic |
| 50 | Federally Qualified Health Center |
| 51 | Inpatient Psychiatric Facility |
| 52 | Psychiatric Facility - Partial Hospitalization |
| 53 | Community Mental Health Center |
| 54 | Intermediate Care Facility/Mentally Retarded |
| 55 | Residential Substance Abuse Treatment Facility |
| 56 | Psychiatric Residential Treatment Center |
| 57 | Non-residential Substance Abuse Treatment Facility |
| 60 | Mass Immunization Center |
| 61 | Comprehensive Inpatient Rehabilitation Facility |
| 62 | Comprehensive Outpatient Rehabilitation Facility |
| 65 | End-Stage Renal Disease Treatment Facility |
| 71 | State or Local Public Health Clinic |
| 72 | Rural Health Clinic |
| 81 | Independent Laboratory |
| 99 | Other Place of Service |

Referring again to FIG. 2, the second dimension in a coded string 202 may be the "service type" dimension 214. As illustrated in the example recoded eligibility response 114A in FIG. 3, an "MM" is provided in the "service type" dimension 214. The "MM" may be a code value for mammogram. "Service type" dimension 214 code values may be derived from various concepts in the healthcare industry. Currently, quantifying a service type into a coded value may include several dimensions. For example, a HIPAA 271 service type code 98 Professions (Physician) Visit—Office may represent a visit/encounter for a professional ("provider type" dimension 216) at an office ("place of service" dimension 212). Embodiments of the present invention provide parsing of the "place of service" dimension 212, the "provider type" dimension 216, and the "reason for service" dimension 222 into different dimensions. A listing of example "service types" and their corresponding code values includes:

| | |
|---|---|
| 101 | Medical |
| 102 | Surgical |
| 103 | Consultation |
| 104 | X-ray |
| 105 | Lab |
| 106 | Radiation |
| 107 | Anesthesia |
| MM | Mammogram |
| VS | Visit |

With reference again to FIG. 2, the third dimension in a coded string 202 may be the "provider type" dimension 216. According to embodiments, "provider type" may be analogous to taxonomy code with an extension of groupings that may not be supported by defined taxonomy codes in use currently. For example, many payers 108 may have benefits that are specific to a specialist; however, there may not be a taxonomy code that bundles all specialists into a single code. Likewise, some payers 108 may wish to clearly delineate a benefit as a facility versus a professional benefit, which is also a grouping that may not be identifiable with a taxonomy code. Referring again to FIG. 3, the example recoded eligibility response 114A does not comprise a code value in the "provider type" dimension 216 of the coded string 202. Accordingly, this may decoded to read that all aspects of the "provider type" dimension 216 may be covered. That is, the patient's plan may cover a particular service with all providers. An example of a message segment 204 comprising a "provider type" dimension 216 code value is illustrated in the example recoded eligibility response 114C. An "SP" is included in the "provider type" dimension 216, which may be decoded as benefits may be provided for services rendered in a specialist's office. A listing of example "provider types" and their associated code values includes:

| | |
|---|---|
| SP | Specialist |
| H | Hospital (generic) |
| HA | Acute Care Hospital |
| C | Chiropractic |
| F | Facility |
| P | Professional |

The fourth dimension in a coded string 202 may be the "relation of provider to payer" dimension 218. With current systems, the "relation of provider to payer" dimension 218 in current EB segments 206 may only support in and out of network relationships. According to embodiments, the "relation of provider to payer" dimension 218 may support network combinations that exist in the healthcare industry, for example, multiple PPO networks. The "relation of provider to payer" dimension 218 in the coded string 202 of the example recoded eligibility response 114A in FIG. 3 includes an "I," which may be decoded as coverage of an in-network (traditional PPO network) relationship. A listing of example "relations of provider to payer" and their corresponding code values includes:

| | |
|---|---|
| I | In network (traditional PPO network) |
| I1 | In network, tier one |
| I2 | In network, tier two |
| O | Out of network |
| A | Applies regardless of the provider's relation to the payer<br>*for deductibles, this may mean there is 1 total deductible for the benefit |
| Blank | Not enough information was sent to know relationship is covered<br>*assumption may be that all relationships apply |

The fifth dimension in a coded string 202 may be the "relation of provider to patient" dimension 220. With current systems (e.g., HIPAA implementation guide), a code to cover various provider to patient relationships may be missing. For example, a code for a relationship of primary care physicians and situations where a patient may be an employee of a hospital may not be included. Currently, payers 108 may insert "relation of provider to patient" information into an eligibility response 112 with a variety of text. Embodiments of the present invention provide a coded value for a provider to patient relationship in the "relation of provider to patient" dimension 220 of a coded string 202 in a message segment 204 of a recoded eligibility response 114. A listing of example "relations of provider to patient" and their corresponding code values includes:

| | |
|---|---|
| P | Primary Care Physician |
| E | Employer |

Referring again to FIG. 3, the "relation of provider to patient" dimension 220 of the example recoded eligibility response 114A does not include a coded value, which may be decoded to read that the requesting healthcare provider 110 is neither a primary care physician to the patient nor an employer of the patient.

The sixth dimension in a coded string 202 may be the "reason for service" dimension 222. Some payers 108 may distinguish between what caused a need for healthcare services to be rendered, for example, illness (sometimes referred to as medical) versus accident. Currently, "reason for service" may be embedded into a "service type" code in an eligibility response 112. Embodiments of the present invention provide segregation of "reason for service" into its own dimension 222, reducing the complexity of the "service type" codes. The "reason for service" dimension 222 of the example recoded eligibility response 114A in FIG. 3 does not include a coded value, which may be interpreted to mean that the payer 108 does not distinguish between what caused the need for the healthcare service to be rendered. A listing of example "reasons for service" and their corresponding code values includes:

| | |
|---|---|
| M | Medically necessary |
| A | Accident |
| I | Injury |
| T | True emergency |
| W | Well care |

The seventh dimension in a coded string 202 may be the "service category" dimension 224. Oftentimes, diagnostic services may have different benefits from screening use of the same service. Currently, the HIPAA "service type" code list may include some multiple entries for each "service category," but may not be complete. Embodiments of the present invention provide a "service category" dimension 224, which may provide a coded value for all combinations of diagnostic and screening service uses. The "service category" dimension 224 of the example recoded eligibility response 114A in FIG. 3 includes a "D," which may be decoded as benefits may be available for diagnostic services. A listing of example "service categories" and their corresponding code values includes:

| | |
|---|---|
| D | Diagnostic |
| S | Screening |

As was mentioned previously, embodiments may remove certain portions of the EB segment 206 and the message segment 204 of the eligibility response 112 in a recoded eligibility response 114. That is, information that is clarified in a coded string 202 in a message segment 204 of a recoded eligibility response 114 may be removed from the EB segment 206 and/or the message segment 204. For example, in the example eligibility response 112E, the EB segment 216 comprises a "98," which may be decoded as professional (Physician) Visit—Office, and which has been removed in the recoded eligibility response 114E. Additionally, the text "This benefit information does not apply to chiropractors" has been removed from the message segment 204 in the recoded eligibility response 114E since this information has been coded into the coded string 202 of the recoded eligibility response 114E.

Figure 4:
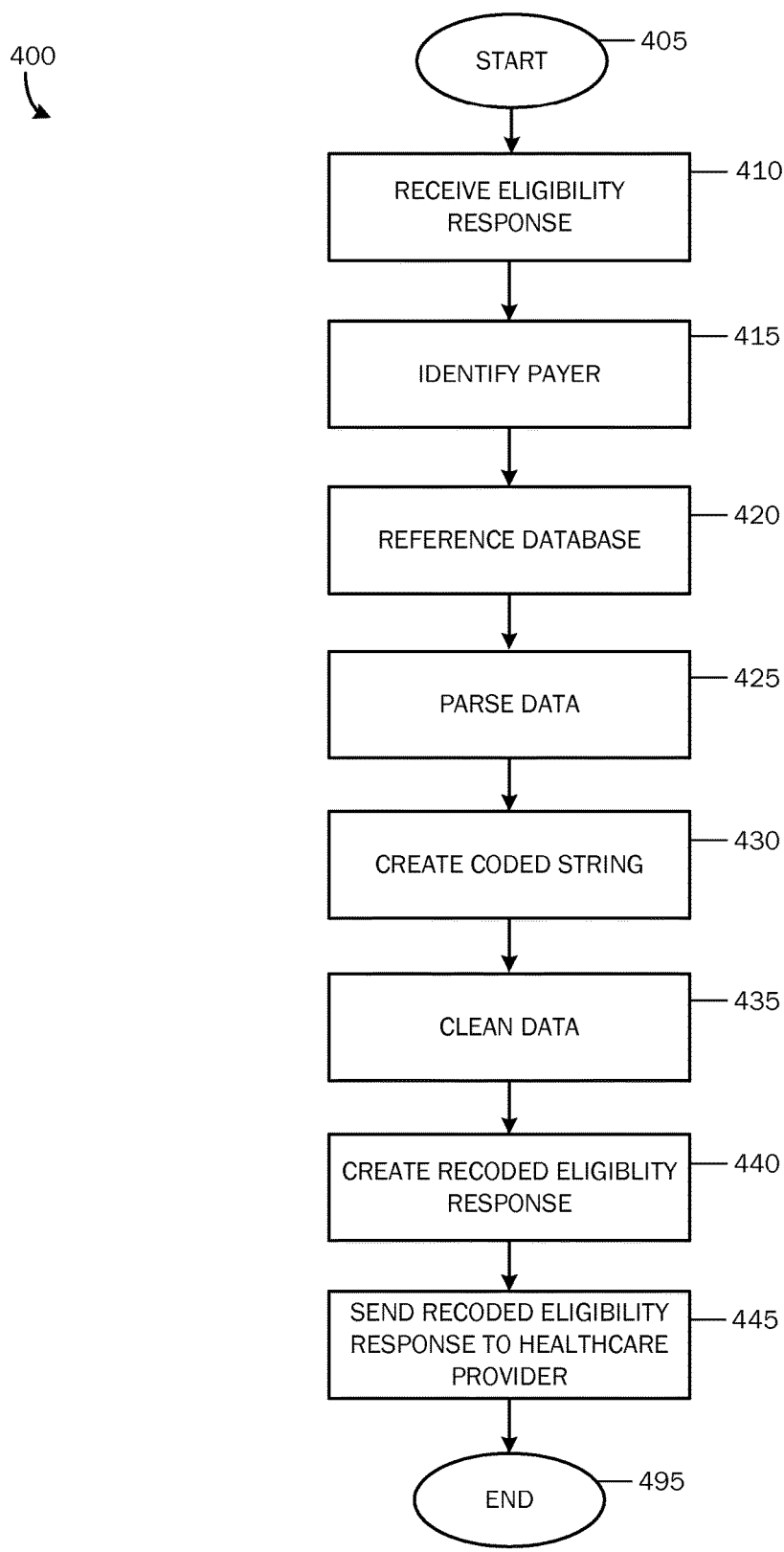
FIG. 4 is a flow chart of a method for providing eligibility response reformatting.

FIG. 4 is a flow chart of a method 400 for providing consistently coded eligibility data. The method 400 starts at OPERATION 405 and proceeds to OPERATION 410, where an eligibility response 112 may be received. As described above, the eligibility response 112 may be sent by a payer 108 in response to an eligibility request 106, for example, a 270 request. The eligibility response 112 may comprise coverage, eligibility, and benefit information coded into various segments of the eligibility response 112.

The method 400 proceeds to OPERATION 415, where the payer 108 from which the eligibility response 112 is received is identified. According to embodiments, depending on the payer 108 sending the response, various pieces of the coverage, eligibility, and benefit information may be coded in a certain format and located in different locations within the eligibility response 112 while still being HIPAA compliant. By identifying which payer 108 sent the response 112, a table 120 may be referenced (OPERATION 420) to look up possible locations to find certain pieces of coverage, eligibility, and benefit information, for example, "place of service" information, "service type" information, "provider type" information, "relation of provider to payer" information, "relation of provider to patient" information, "reason for service" information, and "service category" information. As described above, the table 120 may be generated from historic data. Depending on the payer 108 and with reference to the table 120, only specific pieces of information may need to be recoded. For example, one payer 108 may provide a co-pay amount as a percentage amount, while other payers 108 may provide a co-pay amount as a dollar amount. The table 120 may provide information to notify the coding module 116 to look for the EB segment 206 comprising the co-pay amount as a percentage if the eligibility response 112 is from the specific payer 108.

The method 400 proceeds to OPERATION 425, where the eligibility response 112 is parsed for the specific pieces of information, the locations of which may be provided by the table 120. The information that may be parsed may include one or more of "place of service," "service type," "provider type," "relation of provider to payer," "relation of provider to patient," "reason for service," and "service category" data elements. Message segments may also be parsed for free-form message text identifying critical benefit details and free-form message text identifying benefit details identified in an eligibility benefit segment.

At OPERATION 430, one or more coded strings 202 may be created and provided in one or more message segments 204. As described above, the coded strings 202 may include various code values, each code value representing a dimension of a benefit. According to one embodiment, a coded string 202 may include a tag 208 and one or more of a "place of service" dimension 212, a "service type" dimension 214, a "provider type" dimension 216, a "relation of provider to payer" dimension 218, a "relation of provider to patient" dimension 220, a "reason for service" dimension 222, and a "service category" dimension 224. The coded strings 202 may provide coverage, eligibility, and benefit data in a consistent and standardized format, regardless of the payer 108 sending the eligibility response 112.

At OPERATION 435, a cleaning process may be performed where extraneous data may be filtered out. Message segments 204 that comprise information that is converted to coded data (coded string 202) may be removed from the benefit. For example, an EB segment 206 may include a code for inpatient hospital visit, and a message segment 204 may also be provided that says "inpatient." The cleaning process may filter out one of the redundant pieces of information, providing a cleaner response. Additionally, if a HIPAA service code is recoded into a coded string 202 in a message segment 204, the cleaning process may include removing the HIPAA service code that has been recoded from an EB segment 206.

The method 400 proceeds to OPERATION 440, where a recoded eligibility response 114 may be created. According to embodiments, the recoded eligibility response 114 may include the information provided in the eligibility response 112, but may be cleaned and reformatted into a standardized format. The recoded eligibility response 114 may be sent to a requesting healthcare provider 110 at OPERATION 445. By providing recoded eligibility responses 114, a healthcare provider 110 may be provided with coverage, eligibility, and benefit data in a consistent and standardized form, regardless of the payer 108 sending the eligibility response 112. The method 400 ends at OPERATION 495.

As described above, embodiments of the invention may be implemented via local and remote computing and data storage systems. Such memory storage and processing units may be implemented in a computing device, such as computing device 118 of FIG. 1. Any suitable combination of hardware, software, or firmware may be used to implement the memory storage and processing unit. For example, the memory storage and processing unit may be implemented with computing device 118 or any other computing devices 518, in combination with computing device 118, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 5:
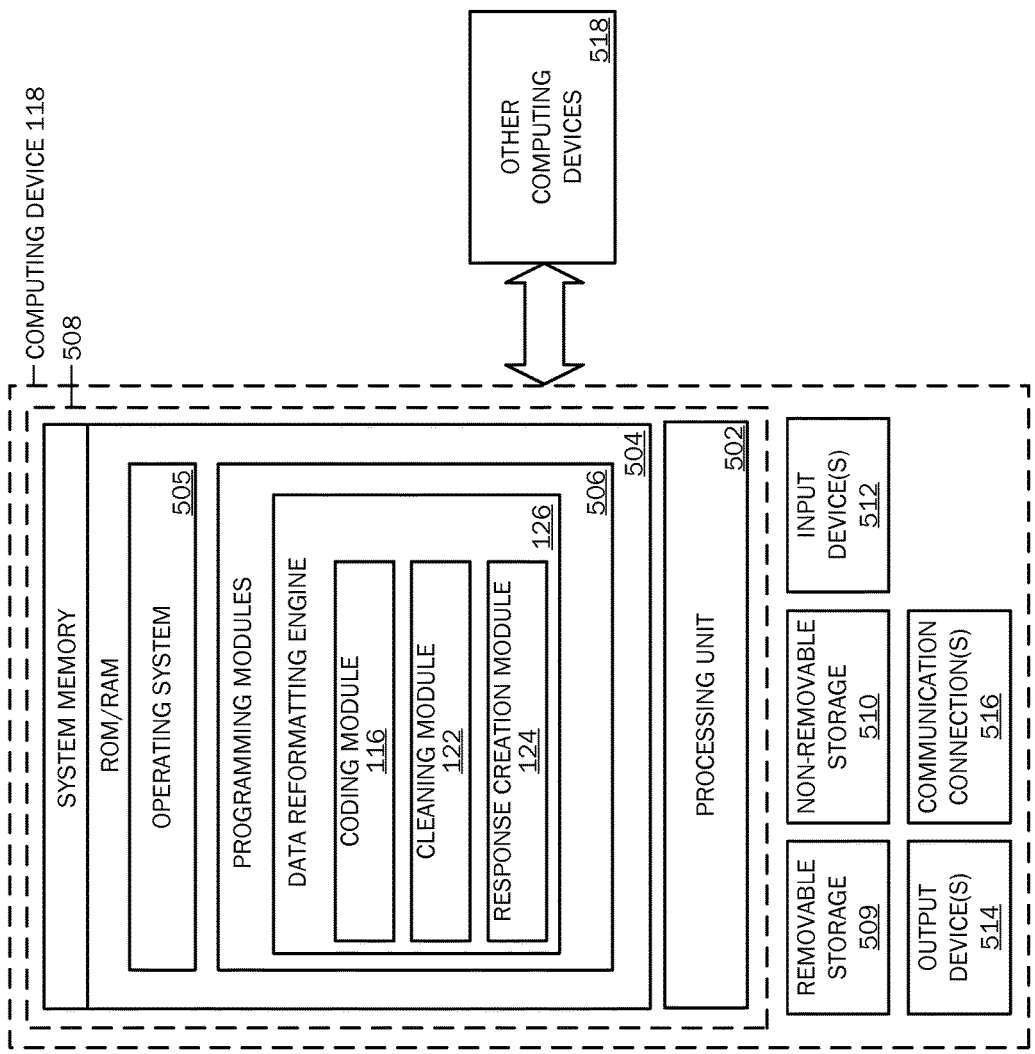
FIG. 5 is a block diagram illustrating example physical components of a computing device with which embodiments of the invention may be practiced.

With reference to FIG. 5, a system consistent with embodiments of the invention may include one or more computing devices, such as computing device 118. The computing device 118 may include at least one processing unit 502 and a system memory 504. The system memory 504 may comprise, but is not limited to, volatile (e.g. random access memory (RAM)), non-volatile (e.g. read-only memory (ROM)), flash memory, or any combination. System memory 504 may include operating system 505, one or more programming modules 506, and may include a coding module 116, a cleaning module 122, and a response creation module 124, wherein the coding module 116, the cleaning module 122, and the response creation module 124 are software applications having sufficient computer-executable instructions, which when executed, performs functionalities as described herein. Operating system 505, for example, may be suitable for controlling computing device 118's operation. Furthermore, embodiments of the invention may be practiced in conjunction with a graphics library, other operating systems, or any other application program and is not limited to any particular application or system. This basic configuration is illustrated in FIG. 5 by those components within a dashed line 508. Computing device 118 may also include one or more input device(s) 512 (keyboard, mouse, pen, touch input device, etc.) and one or more output device(s) 514 (e.g., display, speakers, a printer, etc.).

Although embodiments of the present invention have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages may be recoded in any manner, including by reordering stages and/or inserting or deleting stages, without departing from the invention.

The computing device 118 may also include additional data storage devices (removable and/or non-removable) such as, for example, magnetic disks, optical disks, or tape. Such additional storage is illustrated in FIG. 5 by a removable storage 509 and a non-removable storage 510. Computing device 118 may also contain a communication connection 516 that may allow device 118 to communicate with other computing devices 518, such as over a network in a distributed computing environment, for example, an intranet or the Internet. Communication connection 516 is one example of communication media.

Program modules, such as the coding module 116, the cleaning module 122, and the response creation module 124, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

Embodiments of the present invention, for example, are described above with reference to block diagrams and/or operational illustrations of methods, systems, and computer program products according to embodiments of the invention. For example, each of the FIGS. 1-5 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above.

Rather, the specific features and acts described above are disclosed as example for embodiments of the invention.

We claim:

1. A method of providing a recoded eligibility response as a machine-readable data structure comprising:
receiving, at a computing device that includes a restructuring engine, eligibility data in an original eligibility response;
parsing, by the restructuring engine of the computing device, the eligibility data in the original eligibility response for one or more eligibility benefit data elements and one or more message segments for free-form message text;
removing, by the restructuring engine of the computing device, the free-form message text from the one or more message segments and values of certain eligibility benefit data elements in the original eligibility response;
creating, by the restructuring engine of the computing device, the recoded eligibility response as the machine-readable data structure to include:
a message segment data structure and an eligibility benefit segment data structure, the message segment data structure comprising:
a place of service dimension,
a service type dimension,
a provider type dimension,
a relation of provider to payer dimension,
a relation of provider to patient dimension,
a reason for service dimension, and
a service category dimension;
a coded string to replace removed free-form message text;
one or more coded values for one or more of the place of service dimension, the service type dimension, the provider type dimension, the relation of provider to payer dimension, the relation of provider to patient dimension, the reason for service dimension, and the service category dimension of the message segment data structure;
an embedded tag to indicate a recoding operation for a coded string in a first message segment of the recoded eligibility response when the coded string includes inclusion information; and
an embedded tag to indicate a recoding operation for a coded string in a second message segment of the recoded eligibility response when the coded string includes exclusion information; and
sending, from the computing device, the recoded eligibility response to a requesting healthcare provider computer system.

2. The method of claim 1, further comprising parsing eligibility benefit segments and message segments in the original eligibility response for one or more of:
place of service information;
service type information;
provider type information;
relation of provider to payer information;
relation of provider to patient information;
reason for service information; or
service category information.

3. The method of claim 2, further comprising parsing eligibility benefit segments of the original eligibility response for code values coding one or more of:
place of service information;
service type information;
provider type information;
relation of provider to payer information;
relation of provider to patient information;
reason for service information; or
service category information.

4. The method of claim 2, further comprising parsing the message segments of the original eligibility response for free-form message text identifying critical benefit details.

5. The method of claim 2, further comprising parsing the message segments in the original eligibility response for free-form message text identifying benefit details identified in an eligibility benefit segment and removing the free-form message text from the eligibility benefit segment.

6. The method of claim 2, further comprising:
identifying a payer sending the original eligibility response; and
looking up location information to identify possible locations in the original eligibility response to parse eligibility benefit data elements associated with the payer.

7. The method of claim 1, wherein a coded string codifies one or more of:
place of service information;
service type information;
provider type information;
relation of provider to payer information;
relation of provider to patient information;
reason for service information;
service category information;
free-form message text identifying critical benefit details; or free-form message text identifying benefit details identified in an eligibility benefit segment.

8. The method of claim 1, further comprising recoding the original eligibility response by removing service type information, network indicators, and place of service codes from the original eligibility response.

9. The method of claim 1, further comprising inserting a separator between each dimension of the recoded eligibility response.

10. The method of claim 1, further comprising:
removing eligibility benefit code values, free-form message text identifying critical benefit details, or free-form message text identifying benefit details identified in an eligibility benefit segment that has been codified in a coded string.

11. A system to provide a recoded eligibility response as a machine-readable data structure comprising:
one or more processors;
a restructuring engine comprising executable instructions; and
a memory coupled to the one or more processors, the one or more processors to execute the executable instructions of the restructuring engine to:
receive eligibility data in an original eligibility response;
parse the eligibility data in the original eligibility response for one or more eligibility benefit data elements and one or more message segments for free-form message text
remove the free-form message text from the one or more message segments and values of certain eligibility benefit data elements in the original eligibility response;
create the recoded eligibility response as the machine-readable data structure to include:
a message segment data structure and an eligibility benefit segment data structure, the message segment data structure comprising:
a place of service dimension,
a service type dimension,
a provider type dimension,
a relation of provider to payer dimension, a relation of provider to patient dimension,
a reason for service dimension, and
a service category dimension;
a coded string to replace removed free-form message text;
one or more coded values for one or more of the place of service dimension, the service type dimension, the provider type dimension, the relation of provider to payer dimension, the relation of provider to patient dimension, the reason for service dimension, and the service category dimension of the message segment data structure;
an embedded tag to indicate a recoding operation for a coded string in a first message segment of the recoded eligibility response when the coded string includes inclusion information; and
an embedded tag to indicate a recoding operation for a coded string in a second message segment of the recoded eligibility response when the coded string includes exclusion information; and
provide the recoded eligibility response to a requesting healthcare provider computer system.

12. The system of claim 11, further to parse eligibility benefit segments and message segments in the original eligibility response for one or more of:
place of service information;
service type information;
provider type information;
relation of provider to payer information;
relation of provider to patient information;
reason for service information; or service category information.

13. The system of claim 12, further to parse the eligibility benefit segments for code values coding one or more of:
place of service information;
service type information;
provider type information;
relation of provider to payer information;
relation of provider to patient information;
reason for service information; or
service category information.

14. The system of claim 12 further to parse the message segments for free-form message text identifying critical benefit details and free-form message text identifying benefit details identified in an eligibility benefit segment.

15. The system of claim 12, further to:
identify a payer sending the original eligibility response; and
look up location information to identify possible locations of eligibility benefit data elements in the original eligibility response associated with the payer.

16. The system of claim 11, wherein:
coded values codify one or more of:
place of service information;
service type information;
provider type information;
relation of provider to payer information;
relation of provider to patient information;
reason for service information;
service category information;
free-form message text identifying critical benefit details; or free-form message text identifying benefit details identified in an eligibility benefit segment.

17. The system of claim 11, further to:
remove eligibility benefit code values, free-form message text identifying critical benefit details, or free-form message text identifying benefit details identified in an eligibility benefit segment that has been codified in a coded string; and
provide the recoded eligibility response to a healthcare provider.

18. A non-transitory computer readable medium containing computer executable instructions which, when executed by a computing device, implement a restructuring engine to perform a method of providing a recoded eligibility response as a machine-readable data structure comprising:
receiving eligibility data in an original eligibility response;
parsing, by the restructuring engine, the eligibility data in the original eligibility response for one or more eligibility benefit data elements and one or more message segments for free-form message text;
removing, by the restructuring engine, the free-form message text from the one or more message segments and values of certain eligibility benefit data elements in the original eligibility response;
creating, by the restructuring engine, the recoded eligibility response as the machine-readable data structure to include:
a message segment data structure and an eligibility benefit segment data structure, the message segment data structure comprising:
a place of service dimension,
a service type dimension,
a provider type dimension,
a relation of provider to payer dimension,
a relation of provider to patient dimension,
a reason for service dimension, and
a service category dimension;
a coded string to replace removed free-form message text;
one or more coded values for one or more of the place of service dimension, the service type dimension, the provider type dimension, the relation of provider to payer dimension, the relation of provider to patient dimension, the reason for service dimension, and the service category dimension of the message segment data structure;
an embedded tag to indicate a recoding operation for a coded string in a first message segment of the recoded eligibility response when the coded string includes inclusion information; and
an embedded tag to indicate a recoding operation for a coded string in a second message segment of the recoded eligibility response when the coded string includes exclusion information; and
providing the recoded eligibility response to a requesting healthcare provider computer system.

* * * * *